United States Patent
Stredele et al.

(10) Patent No.: US 6,359,694 B1
(45) Date of Patent: Mar. 19, 2002

(54) METHOD AND DEVICE FOR IDENTIFYING THE POSITION OF AN ELECTRICAL COMPONENT OR TERMINALS THEREOF, AND EQUIPPING HEAD EMPLOYING SAME

(75) Inventors: Bernhard Stredele, Uffing; Stefan Schnellinger; Guenther Wittmann, both of Munich; Hans-Horst Grasmueller, Mammendorf, all of (DE)

(73) Assignee: Siemens Aktiengesellschaft, Munich (DE)

( * ) Notice: Subject to any disclaimer, the term of this patent is extended or adjusted under 35 U.S.C. 154(b) by 0 days.

(21) Appl. No.: 09/078,110

(22) Filed: May 13, 1998

(30) Foreign Application Priority Data

Nov. 10, 1997 (DE) .......................................... 197 49 652

(51) Int. Cl.[7] .............................................. G01N 21/88
(52) U.S. Cl. ...................... 356/614; 356/237.1; 356/394
(58) Field of Search .............................. 356/375, 237.1, 356/394, 614; 29/833, 834, 720

(56) References Cited

U.S. PATENT DOCUMENTS 4,731,649 A * 3/1988 Chang et al. ................ 356/240
5,396,334 A    3/1995 Sugawara
5,519,496 A * 5/1996 Borgert et al. .............. 356/394

FOREIGN PATENT DOCUMENTS

| DE | OS 41 23916 | 1/1992 |
| DE | 44 26 968 | 2/1996 |
| EP | 0 461 395 | 12/1991 |
| EP | 0 243 680 | 4/1994 |
| EP | 0 725 560 | 7/1996 |

* cited by examiner

Primary Examiner—Richard A. Rosenberger
(74) Attorney, Agent, or Firm—Schiff Hardin & Waite

(57) ABSTRACT

In a device and method for detecting the position of components and/or for checking the position of terminals of components, and an insertion head with such a device for detecting the position of components and/or for checking the position of terminals of components, the components are illuminated with vertically incident light, with multi-directional, obliquely incident light, and with horizontally incident light, so that the side surfaces of the components, and thus the projecting terminals as well are sufficiently illuminated. For the horizontal illumination, a light deflection element is employed wherein light is emitted by a light source into the light deflection element, is reflected at a first outer wall of the light deflection element, and is directed into an opening of the light deflection element in which the component is disposed.

7 Claims, 2 Drawing Sheets

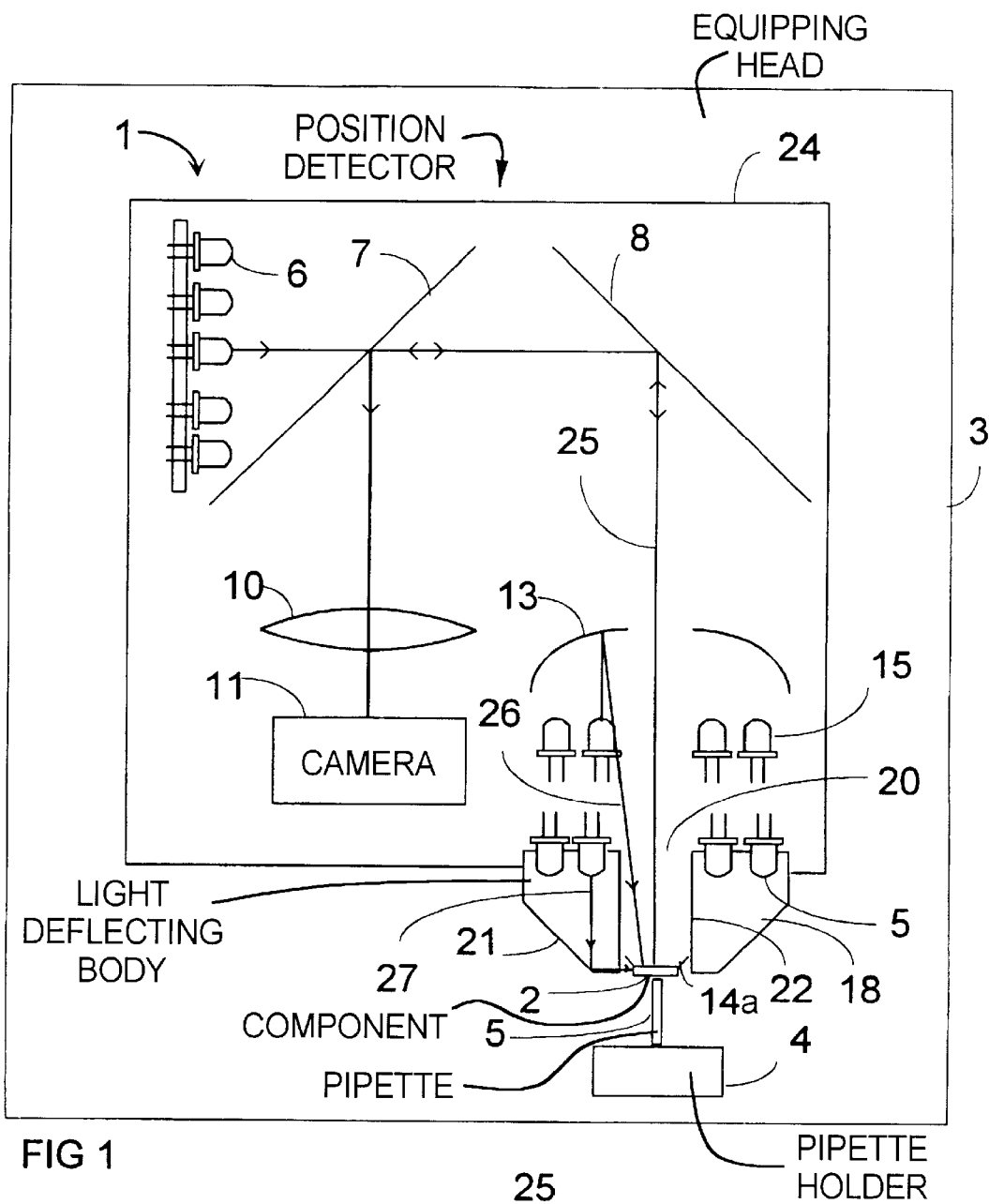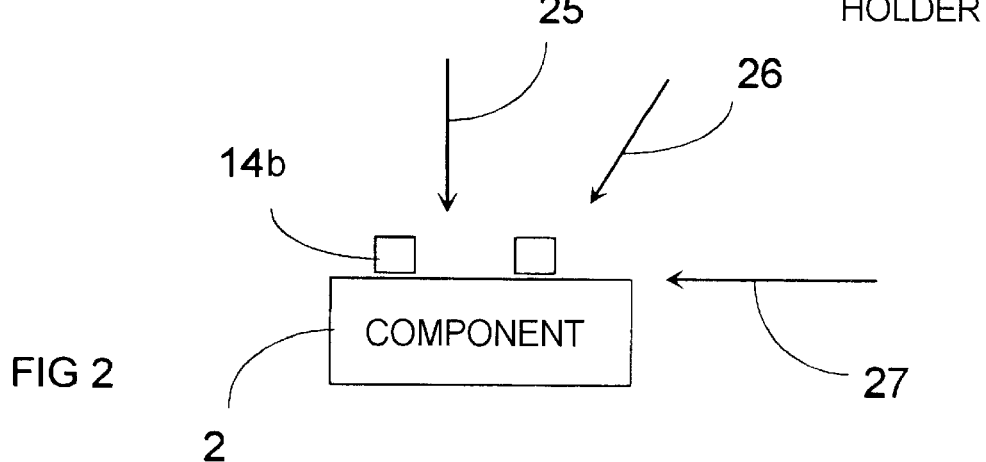

METHOD AND DEVICE FOR IDENTIFYING THE POSITION OF AN ELECTRICAL COMPONENT OR TERMINALS THEREOF, AND EQUIPPING HEAD EMPLOYING SAME

BACKGROUND OF THE INVENTION

1. Field of the Invention

The present invention relates to a method and device for detecting the position of components and/or for checking the position of terminals of components, as well as to an equipping head (component insertion head) having such a device.

2. Description of the Prior Art

In the automatic assembly of circuit boards with components, the components are collected from a delivery means using an equipping (insertion) head and are inserted onto the printed board at positions allocated to the respective components. In order to precisely maintain the position of the component relative to the circuit board, the components are illuminated in a device for position detection, an image of the current position of the component at the equipping head is taken using a camera, and this is compared with a prescribed position in an image evaluation unit connected downstream to the camera. The equipping head subsequently transports the component to the prescribed position on the circuit board, dependent on the current position. For the assembly of components without housings and with terminals which are distributed in two dimensions over the entire surface of the component (flip-chip assembly), the position detection is performed using the terminal positions.

European Application 0 243 680 teaches a device for exposure illumination, including means for the simultaneous striking the surface of the circuit board with vertically incident beams and multi-directional, obliquely incident beams, in order to detect the position of interconnects or adjusting structures on circuit boards. The terms "vertical," and "horizontal," are referenced to the surface of the component, which lies essentially perpendicularly to the optical axis of the imaging. The terminals in the flip-chip assembly are poorly illuminated and cannot be clearly recognized in the image evaluation unit in this known device.

German OS 44 26 968 teaches a light conductor which can be used for the lateral illumination of an object. The light conductor has walls at which the light reflected by the side surfaces of the object can be deflected to an optical inspection system. The side surfaces and the top of the object under observation thus can be optically checked. Reflective surface structures are very difficult to detect by means of the laterally incident light, and such a separate light conductor can be integrated into an insertion process only with difficulty.

SUMMARY OF THE INVENTION

It is an object of the present invention to provide a device and method to detect the position and/or to check the position of the terminals of components, wherein not only laterally projecting structures, but also surface structures of components and their terminals are sufficiently illuminated, such that the position of the terminals of the components at an equipping head can be reliably detected by a camera with image evaluation unit connected downstream.

The above object is achieved in accordance with the principles of the present invention in an illumination device wherein a component, having a planar surface and side surfaces from which terminals extend, is illuminated with light in a direction normal to the planar surface from a first light source, and is simultaneously illuminated with multi-directional, obliquely incident light from a second light source, and is simultaneously illuminated with light proceeding substantially parallel to the planar surface (i.e., illuminating the sides of the component) from a third light source.

If the aforementioned planar surface of the component is horizontally oriented, then the light from the first light source proceeds vertically and the light from the third light source proceeds horizontally.

In a device constructed as described above, and in a method proceeding as described above, not only can reflective surface structures be illuminated, but also laterally projecting terminals are illuminated.

In a preferred embodiment of the method and device, the vertically incident light is created by light sources which couple their light in through a semi-reflective mirror in the radiation path of a single illumination element. An imaging of the component onto a camera ensues by a reflection at the semi-reflective mirror.

The second light source for illuminating the component with multi-directional, obliquely incident light can be a mirror arrangement. This is particularly simple compared to the use of optical lens systems and can be integrated into the illumination device in a compact fashion.

The third light source for illuminating the component with horizontally incident light can be a light deflection element which deflects the light incident thereon onto the side surfaces of the component, the component being located in an opening of the light deflection element. The structures which protrude laterally from the component thus can be easily recognized from above and used for position detection.

Each of the light sources for illumination with vertically incident light, with multi-directional, obliquely incident light, and with horizontally incident light can be formed by light-emitting diodes.

The light deflection element can be manufactured from an optically transparent plastic.

The light sources can be arranged in holding devices of the light deflection element provided therefor, which produces a good fixing of the light sources with a simultaneous low loss of light performance.

In a preferred embodiment, the light deflection element has recesses through which the components are transported into the opening essentially horizontally, and thus without a vertical motion which is more costly to produce from a technical standpoint.

A particularly high insertion performance is achieved with an insertion head having the illumination device attached thereto, because the insertion head then need not approach a particular means for position detection within the insertion machine for every position detection.

DESCRIPTION OF THE DRAWINGS

FIG. 1 is a schematic cross-section through an inventive device for position detection.

FIG. 2 is a schematic depiction of the various illumination types employed in the inventive device.

DESCRIPTION OF THE PREFERRED EMBODIMENTS

Figure 3:
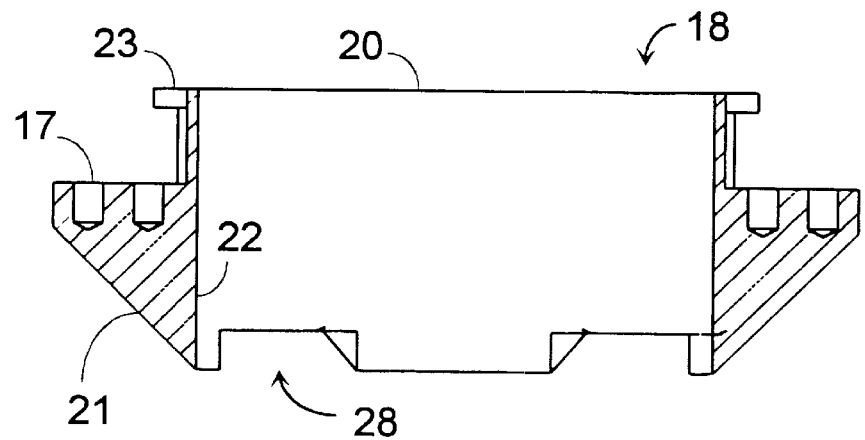
FIG. 3 is a schematic cross-section through a light deflection body constructed in accordance with the principles of the present invention, taken along line IV—IV of FIG. 4.

FIG. 1 depicts a position detector 1 for detecting the position and/or checking the position of the terminals 14 of a component 2. The position detector 1 is preferably secured at an equipping head 3 of an insertion machine. The equipping head 3 also has a rotatably mounted suction pipette holder 4 (revolver head) with at least one suction pipette 5 for taking the component 2 from a delivery means (not shown). The position detector 1 has a first arrangement for illuminating a component 2 with vertical light incidence from above, wherein surfaces of the component 2 which reflect particularly well, such as terminals 14a (FIG. 1) or interconnects or 14b (FIG. 2), for example, are recognized, these having a planar surface. For this type of illumination, a first light source is provided which is formed by a first group of light emitting diodes 6 whose emitted light is deflected through a first mirror 7, which is semi-reflective designed which is semi-reflective, and by reflection at a second mirror 8, vertically onto the surface of the component 2. The imaging of the illuminated component 2 ensues likewise via the second mirror 8 and the semi-reflective mirror 7, which image the component via an optical imaging element 10, e.g. an objective lens, onto a camera 11 in the position detector 1 for position detection. The camera 11 is connected with an image evaluation unit (not shown) in which the position of the component 2 at the equipping head 3 is determined in relation to a prescribed target position. In addition, a second arrangement for illumination of the component 2 with multi-directional, obliquely incident light is provided. This second arrangement has a second light source which is formed by a second group of light emitting diodes 12 and a third mirror arrangement 13 which deflects the light emitted by the second light source so that it strikes the component 2 in a multi-directional, oblique fashion. The imaging again ensues onto the camera 11 via the second mirror 8 and the semi-reflective mirror 7.

Furthermore, a third arrangement for illumination of the component 2 with horizontally incident light 27 falling on the side surfaces of the component 2 is provided, so that structures protruding laterally from the component 2, such as terminals 14, are recognized. FIG. 2 depicts the three illumination types again in a clearer fashion. The third arrangement has a third light source in the form of a third group of light emitting diodes 16 which are secured in holding devices 17 of a light deflection body 18. The light deflection body 18 is formed by a transparent material such as glass or optically transparent plastic (PC, polycarbonate, Makralon® or PMMA, polymethacrylate, Plexiglas®). The light emitted by the third group of light emitting diodes 16 is deflected in the light deflection body 18 onto the side surfaces of the component 2 located in an opening 20 of the light deflection body 18. The imaging ensues likewise onto the camera 11 via the second mirror 8 and the semi-reflective mirror 7. Instead of the light deflection body 18, a fourth mirror arrangement (not shown) for deflecting the light into the horizontal plane can be used.

Figure 4:
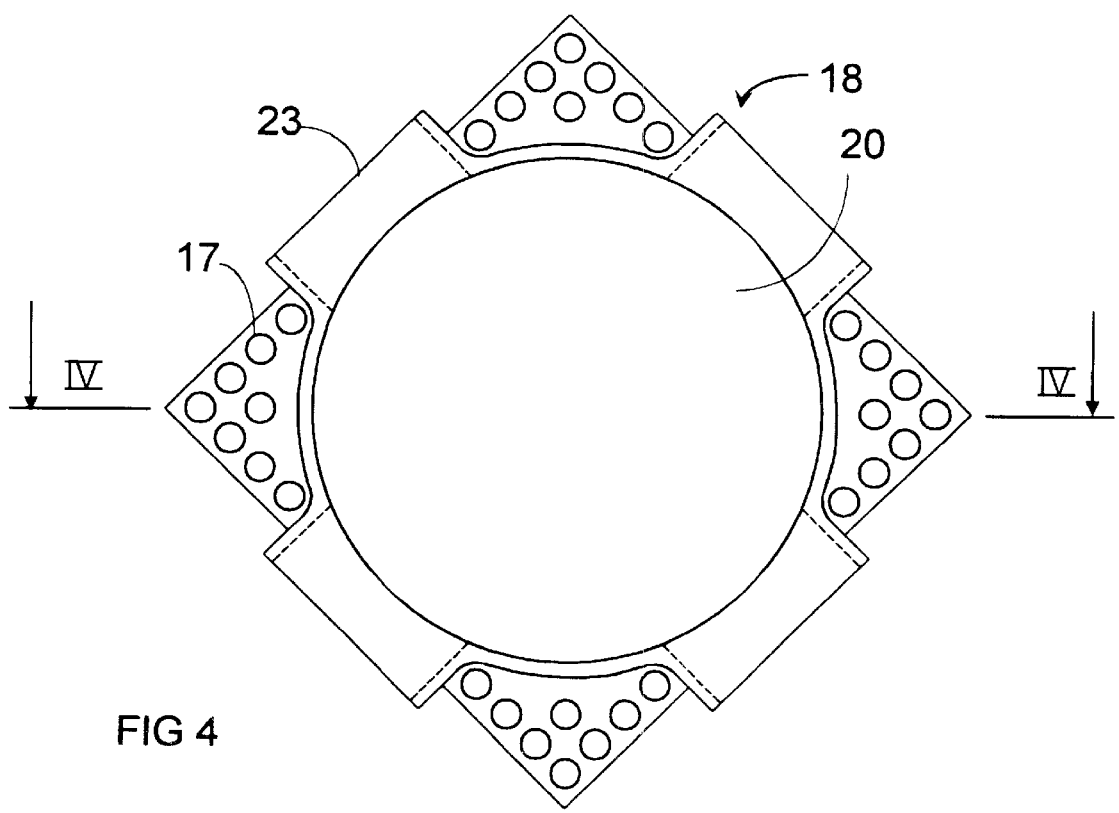
FIG. 4 is a plan view of a light deflection body constructed in accordance with the principles of the present invention.

The light deflection body 18 is shown in greater detail in the plan view of FIG. 4 and in the section along the edge A—A in FIG. 3. The third group of light emitting diodes 16 is secured in the holding devices 17 which are designed as boreholes. These emit light into the light deflection body 18, wherein the light is reflected by total reflection at a first (outer) wall 21 and proceeds through a second (inner) wall 22 into the opening 20 of the light deflection body 18—and thus onto the side surfaces of the component 2. The light deflection body 18 also has fixing devices 23 with which it is detachably secured in the housing 24 of the device 1 for position detection. Not only the vertically incident light from above, but also the multi-directional, obliquely incident light reaches the component 2 through the opening 20. The imaging onto the camera 11 likewise ensues through the opening 20 of the light deflection body 18. The light deflection body 18 has recesses 28 for the essentially horizontal transport of the component 2 into the opening 20. A technically costly vertical motion of the component 2 is thus avoided.

The arrangement with mirrors (7, 8, 13) and light emitting diodes (6, 12, 15) is especially simple and space-efficient and thus can be secured to an insertion head 3. This results in a large time savings in insertion, since a separate station for position detection need not be approached. The insertion performance (throughput) of the insertion machine thereby increases.

Although modifications and changes may be suggested by those skilled in the art, it is the intention of the inventors to embody within the patent warranted hereon all changes and modifications as reasonably and properly come within the scope of their contribution to the art.

We claim as our invention:

1. A device for identifying a position of an object selected from the group consisting of electrical components and terminals of electrical components, said object having a planar surface, said device comprising:

first illumination arrangement for illuminating said planar surface of said object with light incident in a direction normal to said planar surface and producing reflected light;

second illumination arrangement for illuminating said object with multi-directional light which is obliquely incident on said planar surface and producing reflected light;

third illumination arrangement for illuminating said object with non-diffusive light in a direction substantially parallel to said surface and producing reflected light, said third illumination means comprising a light source and a light deflecting body, through which light from said light source passes, said light deflecting body presenting rotation symmetry and having a body wall which deflects said light from said light source passing through said body on to said object in said direction substantially parallel to said planar surface; and a single light detector comprising a camera for obtaining and evaluating an image of said object while simultaneously illuminated by said first illumination arrangement, said second illumination arrangement and said third illumination arrangement, said image consisting exclusively of the reflected light produced by said first illumination arrangement, said second illumination arrangement and said third illumination arrangement.

2. A device as claimed in claim 1, wherein said light source comprises a group of light-emitting diodes.

3. A device as claimed in claim 2, wherein said light-emitting diodes are disposed in said light deflecting body.

4. A device as claimed in claim 1, wherein said body wall comprises an exterior wall of said light deflecting body, and wherein said light deflecting body has an interior opening in which said object is disposed, said interior opening having an interior body wall and said light from said light source being deflected by said exterior body wall through said interior body wall onto said object.

5. A device as claimed in claim 4, wherein said light deflecting body comprises at least one axis opening, communicating with said interior opening, through which said object can be conveyed from an exterior of said light deflecting body into said interior opening in said direction substantially parallel to said planar surface.

6. A device as claimed in claim 1, wherein said light deflecting body is comprised of optically transparent plastic.

7. A method for detecting a position of an object having a planar surface, the method comprising the steps of:

illuminating said object with light proceeding from a first light source onto said object in a direction normal to said planar surface;

simultaneously illuminating said object with light from a second light source proceeding multi-directionally and being obliquely incident on said planar surface;

simultaneously illuminating said object with non-diffusive light from a third light source proceeding substantially parallel to said planar surface, said third light source comprising a light source and a light deflecting body, through which light from said third light source passes, said light deflecting body presenting rotation symmetry and having a body wall which deflects said light from said third light source passing through said body onto said object in said direction substantially parallel to said planar surface; and obtaining an image of said object while simultaneously illuminated by said light from the respective first, second and third light sources, and evaluating said image to identify a position of at least a portion of said object.

\* \* \* \* \*